US011610344B2

(12) United States Patent
Morita

(10) Patent No.: US 11,610,344 B2
(45) Date of Patent: Mar. 21, 2023

(54) IMAGE INTERPRETATION SUPPORT APPARATUS, IMAGE INTERPRETATION SUPPORT METHOD, AND IMAGE INTERPRETATION SUPPORT PROGRAM

(71) Applicant: FUJIFILM Corporation, Tokyo (JP)

(72) Inventor: Junya Morita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 219 days.

(21) Appl. No.: 16/899,427

(22) Filed: Jun. 11, 2020

(65) Prior Publication Data
US 2020/0394827 A1    Dec. 17, 2020

(30) Foreign Application Priority Data

Jun. 13, 2019   (JP) .............................. JP2019-110465

(51) Int. Cl.
G06T 11/00    (2006.01)
G16H 15/00    (2018.01)
(Continued)

(52) U.S. Cl.
CPC ............ *G06T 11/005* (2013.01); *A61B 6/025* (2013.01); *A61B 6/502* (2013.01); *A61B 6/5217* (2013.01);
(Continued)

(58) Field of Classification Search
None
See application file for complete search history.

(56) References Cited

U.S. PATENT DOCUMENTS 8,983,156 B2   3/2015 Periaswamy et al.
2006/0100507 A1   5/2006 Mertelmeier
(Continued)

FOREIGN PATENT DOCUMENTS

JP   2006-116313 A   5/2006
JP   2011-110430 A   6/2011
(Continued)

OTHER PUBLICATIONS

Chan Heang-Ping et al.; "Computer-aided detection of masses in digital tomosynthesis mammography: Comparison of three approaches"; Medical Physics; AIP; Aug. 14, 2008; pp. 4087-4095; vol. 35; No. 9; XP012116242; Melville, NY, U.S.
(Continued)

*Primary Examiner* — Samah A Beg
*Assistant Examiner* — Courtney Joan Nelson
(74) *Attorney, Agent, or Firm* — Studebaker & Brackett PC

(57) ABSTRACT

An image interpretation support apparatus includes: an acquisition unit that acquires a plurality of projection images obtained by tomosynthesis imaging in which a radiation is irradiated to a breast from different irradiation angles by a radiation source and a projection image is captured at each irradiation angle by a radiation detector; a first generation unit that generates a plurality of tomographic images on each of a plurality of tomographic planes of the breast from the plurality of projection images; a second generation unit that generates a synthetic two-dimensional image from a plurality of images among the plurality of projection images and the plurality of tomographic images; a detection unit that detects an object of interest candidate region estimated to include an object of interest from the synthetic two-dimensional image; and a determination unit that determines whether or not the object of interest is included in the object
(Continued)

of interest candidate region on the basis of the plurality of tomographic images.

17 Claims, 11 Drawing Sheets

(51) Int. Cl.
*G16H 30/20* (2018.01)
*G16H 50/70* (2018.01)
*G16H 50/20* (2018.01)
*G16H 30/40* (2018.01)
*A61B 6/02* (2006.01)
*A61B 6/00* (2006.01)
*G06T 7/00* (2017.01)

(52) U.S. Cl.
CPC ........... *G06T 7/0012* (2013.01); *G16H 15/00* (2018.01); *G16H 30/20* (2018.01); *G16H 30/40* (2018.01); *G16H 50/20* (2018.01); *G16H 50/70* (2018.01); *G06T 2207/10112* (2013.01); *G06T 2207/30068* (2013.01)

(56) References Cited

U.S. PATENT DOCUMENTS

| | | | |
|---|---|---|---|
| 2008/0025592 A1* | 1/2008 | Jerebko | ................ G06T 11/005 382/132 |
| 2009/0123052 A1 | 5/2009 | Ruth et al. | |
| 2011/0123089 A1 | 5/2011 | Bertens et al. | |
| 2012/0069951 A1 | 3/2012 | Toba | |
| 2014/0198965 A1* | 7/2014 | Woods | ................ G06T 7/0012 382/131 |
| 2015/0269766 A1 | 9/2015 | Kobayashi | |
| 2016/0095563 A1 | 4/2016 | Fukuda et al. | |
| 2018/0033143 A1* | 2/2018 | Buelow | ................ G06T 7/0014 |
| 2019/0043456 A1 | 2/2019 | Kreeger et al. | |
| 2020/0214658 A1 | 7/2020 | Otomaru et al. | |

FOREIGN PATENT DOCUMENTS

| | | |
|---|---|---|
| JP | 2012-061196 A | 3/2012 |
| JP | 2014128716 A | 7/2014 |
| JP | 2014-534042 A | 12/2014 |
| JP | 2015-177928 A | 10/2015 |
| JP | 6208731 B2 | 10/2017 |
| JP | 2018-512913 A | 5/2018 |
| JP | 2019-063504 A | 4/2019 |
| WO | 2014/203531 A1 | 12/2014 |

OTHER PUBLICATIONS

The extended European search report issued by the European Patent Office dated Nov. 9, 2020, which corresponds to European Patent Application No. 20179572.1-1122 and is related to U.S. Appl. No. 16/899,427.

An Office Action mailed by the Japanese Patent Office dated Aug. 2, 2022, which corresponds to Japanese Patent Application No. 2019-110465 and is related to U.S. Appl. No. 16/899,427.

An Office Action mailed by the Japanese Patent Office dated Nov. 1, 2022, which corresponds to Japanese Patent Application No. 2019-110465 and is related to U.S. Appl. No. 16/899,427.

* cited by examiner

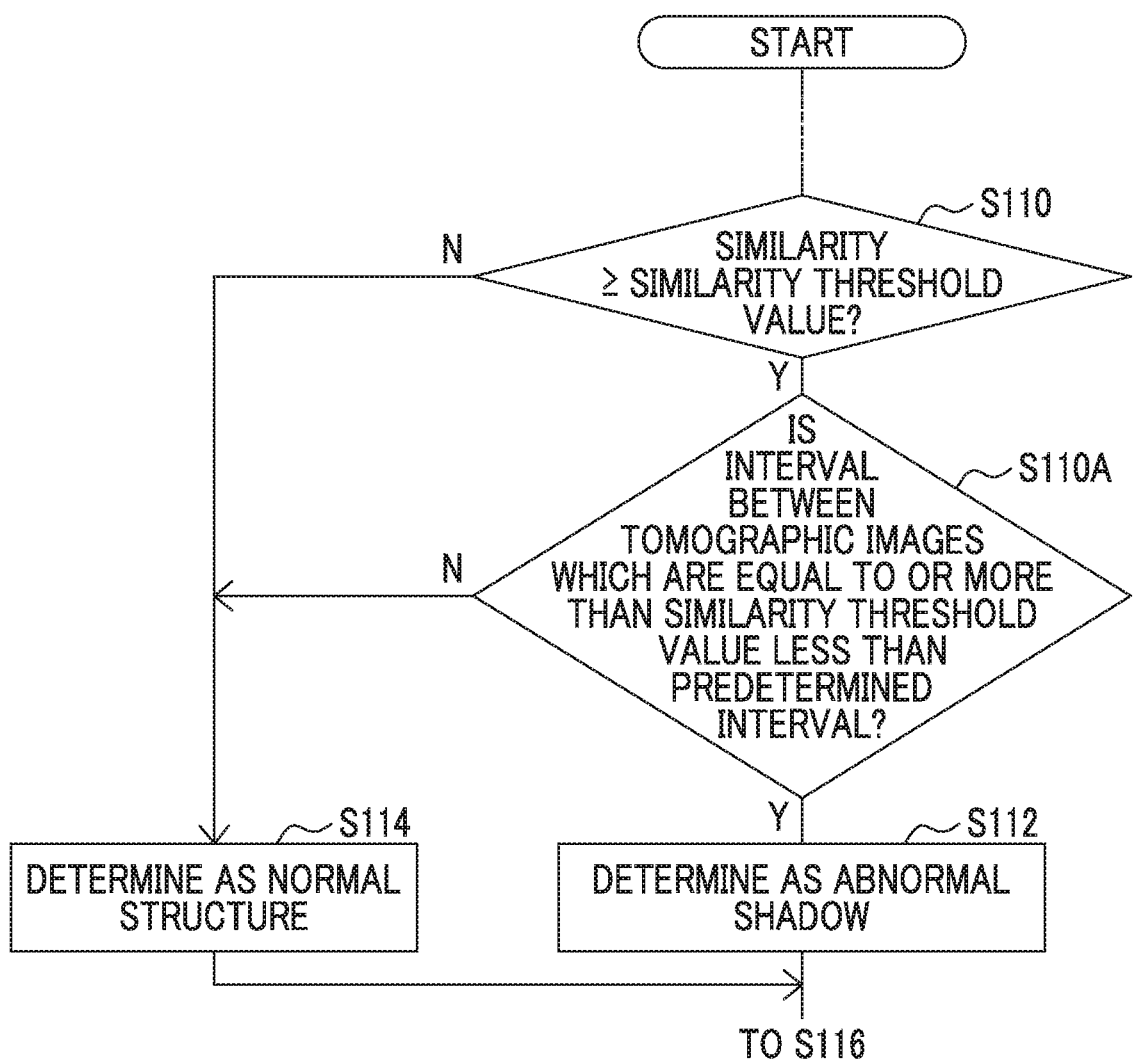

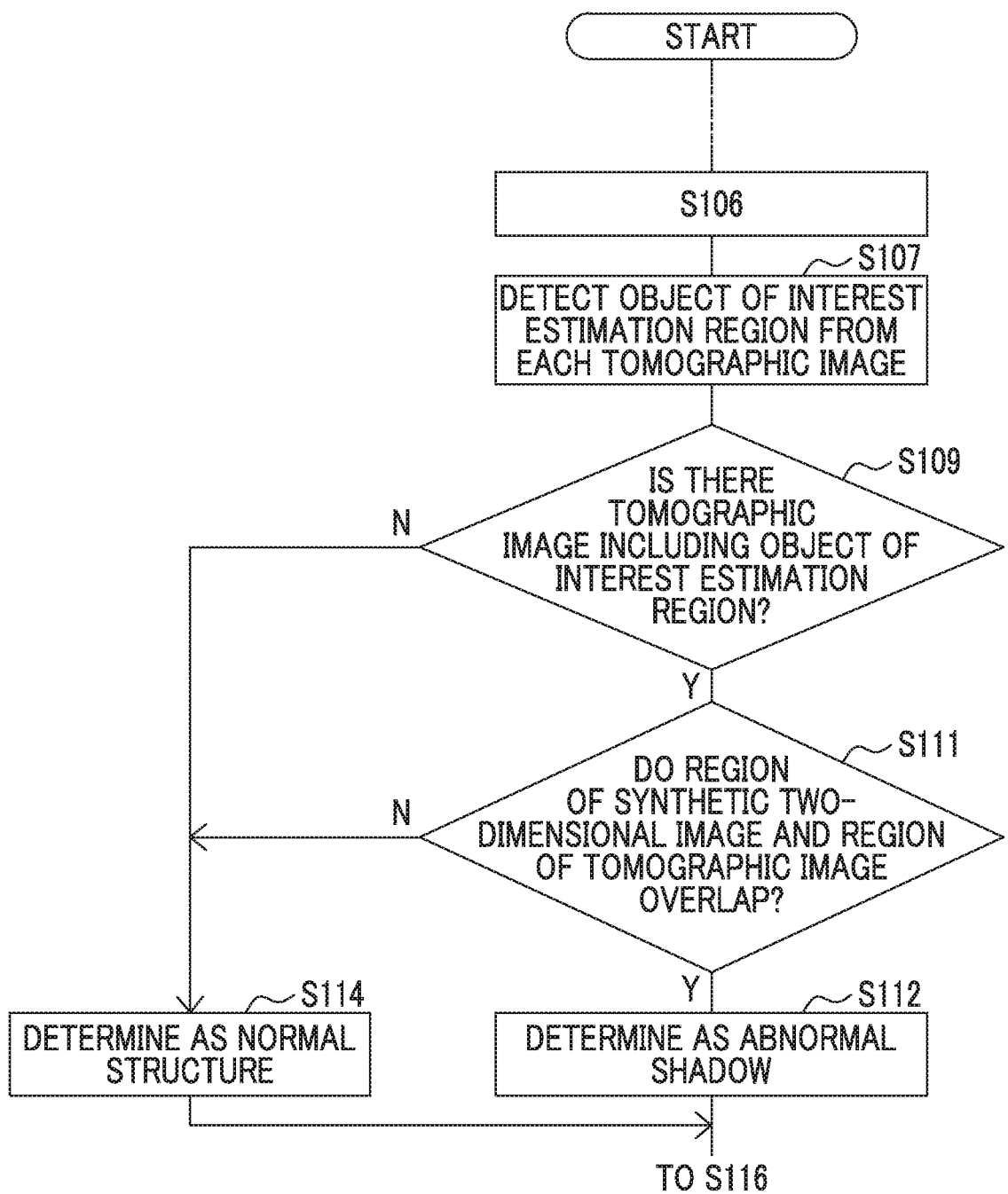

IMAGE INTERPRETATION SUPPORT APPARATUS, IMAGE INTERPRETATION SUPPORT METHOD, AND IMAGE INTERPRETATION SUPPORT PROGRAM

CROSS-REFERENCE TO RELATED APPLICATIONS

The present application claims priority under 35 U.S.C. § 119 to Japanese Patent Application No. 2019-110465 filed on Jun. 13, 2019. The above application is hereby expressly incorporated by reference, in its entirety, into the present application.

BACKGROUND

1. Technical Field

The present invention relates to an image interpretation support apparatus, an image interpretation support method, and an image interpretation support program

2. Description of the Related Art

In general, a technique is known in which a doctor or the like interprets a radiographic image captured by a mammography apparatus, thereby diagnosing a breast lesion or the like. As this kind of radiographic image, a plurality of projection images obtained by so-called tomosynthesis imaging and a tomographic image generated by reconstructing the plurality of projection images are known. Further, as the main radiographic image, a synthetic two-dimensional image generated from a plurality of images selected from the plurality of projection images and a plurality of tomographic images is known.

For example, JP6208731B discloses a method of generating the synthetic two-dimensional image by reconstructing the plurality of tomographic images, or the plurality of images including at least one of the tomographic image or the projection image by any method such as a filtered back projection method, a maximum likelihood reconstruction method, an iterative reconstruction method, a reconstruction method using an algebraic method, or a three-dimensional reconstruction method.

Further, for example, U.S. Pat. No. 8,983,156B discloses a method of blending (synthesizing) a region of interest (ROI) detected from the tomographic image with a two-dimensional image to generate the synthetic two-dimensional image.

SUMMARY

In the techniques disclosed in JP6208731B and U.S. Pat. No. 8,983,156B, it is difficult to perform diagnosis and the like only with the synthetic two-dimensional image, and there are cases where it is necessary to perform an interpretation of other radiographic images such as the tomographic images, and thus the number of images to be interpreted increases. As the number of images to be interpreted increases, an interpretation time increases.

The present disclosure has been made in view of the above-mentioned problems and an object of the present disclosure is to provide an image interpretation support apparatus, an image interpretation support method, and an image interpretation support program that can effectively perform an interpretation of a radiographic image.

In order to achieve the object, according to a first aspect of the present disclosure, there is provided an image interpretation support apparatus comprising: an acquisition unit that acquires a plurality of projection images obtained by tomosynthesis imaging in which radiation is irradiated to a breast from different irradiation angles by a radiation source and a projection image is captured at each irradiation angle by a radiation detector, a first generation unit that generates a plurality of tomographic images on each of a plurality of tomographic planes of the breast from the plurality of projection images, a second generation unit that generates a synthetic two-dimensional image from a plurality of images among the plurality of projection images and the plurality of tomographic images, a detection unit that detects an object of interest candidate region estimated to include an object of interest from the synthetic two-dimensional image, and a determination unit that determines whether or not the object of interest is included in the object of interest candidate region on the basis of the plurality of tomographic images.

According to a second aspect of the present disclosure, in the image interpretation support apparatus according to the first aspect, the determination unit determines whether or not the object of interest is included in the object of interest candidate region on the basis of a comparison result obtained by comparing an image of the object of interest candidate region in the synthetic two-dimensional image and an image of a corresponding region corresponding to the object of interest candidate region in the tomographic image.

According to a third aspect of the present disclosure, the image interpretation support apparatus according to the second aspect, in a case where similarity between the image of the corresponding region in each of the plurality of tomographic images and the image of the object of interest candidate region is less than similarity threshold value, the determination unit determines that the object of interest is not included in the object of interest candidate region.

According to a fourth aspect of the present disclosure, the image interpretation support apparatus according to the second aspect, in a case where the plurality of tomographic images include a tomographic image in which similarity between the image of the corresponding region and the image of the object of interest candidate region is equal to or more than similarity threshold value, the determination unit determines that the object of interest is included in the object of interest candidate region.

According to a fifth aspect of the present disclosure, the image interpretation support apparatus according to the third aspect, in a case where the plurality of tomographic images include a tomographic image in which the similarity is equal to or more than the similarity threshold value, the determination unit performs a control to cause the second generation unit to generate a regenerated synthetic two-dimensional image resynthesized from the plurality of images including at least the tomographic image in which the similarity is equal to or more than the similarity threshold value and having a weight of the tomographic image in which the similarity is equal to or more than the similarity threshold value larger than those of other images.

According to a sixth aspect of the present disclosure, the image interpretation support apparatus according to the first aspect, the detection unit further detects an object of interest estimation region estimated to include the object of interest from each of the plurality of tomographic images, and the determination unit determines whether or not the object of interest is included in the object of interest candidate region on the basis of a position of the object of interest candidate region with respect to an image of the breast in the synthetic two-dimensional image and a position of the object of interest estimation region with respect to an image of the breast in the tomographic image.

According to a seventh aspect of the present disclosure, the image interpretation support apparatus according to the sixth aspect, in a case where the object of interest estimation region is not detected from each of the plurality of tomographic images, or in a case where the object of interest candidate region does not overlap with the object of interest estimation region, the determination unit determines that the object of interest is not included in the object of interest candidate region.

According to an eighth aspect of the present disclosure, the image interpretation support apparatus according to the sixth aspect, the determination unit determines that the object of interest is included in the object of interest candidate region in a case where at least a part of the object of interest candidate region or the object of interest estimation region overlap each other.

According to a ninth aspect of the present disclosure, the image interpretation support apparatus according to the sixth aspect, in a case of including a tomographic image in which at least a part of the object of interest estimation region overlaps with the object of interest candidate region, the determination unit performs a control to cause the second generation unit to generate a regenerated synthetic two-dimensional image resynthesized from the plurality of images including at least the tomographic image in which the at least a part of the object of interest estimation region overlaps with the object of interest candidate region, and having a weight of the tomographic image in which at least the part overlaps with the object of interest candidate region larger than other images.

According to a tenth aspect of the present disclosure, the image interpretation support apparatus according to the fifth aspect, the determination unit performs a control to cause a display unit to display the regenerated synthetic two-dimensional image which is resynthesized.

According to an eleventh aspect of the present disclosure, the image interpretation support apparatus according to the first aspect and the sixth to eighth aspects, in a case where the determination unit determines that the object of interest is included in the object of interest candidate region, the determination unit sets a contrast of the object of interest candidate region in the synthetic two-dimensional image to be stronger than contrasts of other regions.

According to a twelfth aspect of the present disclosure, the image interpretation support apparatus according to the first aspect, in a case where the determination unit determines that the object of interest is not included in the object of interest candidate region, the determination unit sets a contrast of the object of interest candidate region in the synthetic two-dimensional image to be weaker than contrasts of other regions.

According to a thirteenth aspect of the present disclosure, the image interpretation support apparatus according to the first aspect and the sixth to eighth aspects, in a case where the determination unit determines that the object of interest is included in the object of interest candidate region, the determination unit sets a pixel value of a pixel in which a degree of an object of interest representing a likelihood of the object of interest is equal to or more than a degree threshold value to be larger than pixel values of other pixels among pixels of the object of interest candidate region.

According to a fourteenth aspect of the present disclosure, the image interpretation support apparatus according to the first aspect and the thirteenth aspect, in a case where the determination unit determines that the object of interest is not included in the object of interest candidate region, the determination unit sets a pixel value of a pixel in which a degree of an object of interest representing a likelihood of the object of interest is equal to or more than a degree threshold value to be smaller than pixel values of other pixels among pixels of the object of interest candidate region.

Further, in order to achieve the object, according to a fifteenth aspect of the present disclosure, there is provided an image interpretation support method executed by a computer, the method comprising: acquiring a plurality of projection images obtained by tomosynthesis imaging in which radiation is irradiated to a breast from different irradiation angles by a radiation source and a projection image is captured at each irradiation angle by a radiation detector, generating a plurality of tomographic images on each of a plurality of tomographic planes of the breast from the plurality of projection images, generating a synthetic two-dimensional image from a plurality of images among the plurality of projection images and the plurality of tomographic images, detecting an object of interest candidate region estimated to include an object of interest from the synthetic two-dimensional image, and determining whether or not the object of interest is included in the object of interest candidate region on the basis of the plurality of tomographic images.

Further, in order to achieve the object, according to a sixteenth aspect of the present disclosure, there is provided a non-transitory computer-readable storage medium storing an image interpretation support program for causing a computer to execute a process, the process comprising: acquiring a plurality of projection images obtained by tomosynthesis imaging in which radiation is irradiated to a breast from different irradiation angles by a radiation source and a projection image is captured at each irradiation angle by a radiation detector, generating a plurality of tomographic images on each of a plurality of tomographic planes of the breast from the plurality of projection images, generating a synthetic two-dimensional image from a plurality of images among the plurality of projection images and the plurality of tomographic images, detecting an object of interest candidate region estimated to include an object of interest from the synthetic two-dimensional image, and determining whether or not the object of interest is included in the object of interest candidate region on the basis of the plurality of tomographic images.

An image interpretation support apparatus according to the present disclosure is an image interpretation support apparatus including a processor. The processor acquires a plurality of projection images obtained by tomosynthesis imaging in which radiation is irradiated to a breast from different irradiation angles by a radiation source and a projection image is captured at each irradiation angle by a radiation detector, generates a plurality of tomographic images on each of a plurality of tomographic planes of the breast from the plurality of projection images, generates a synthetic two-dimensional image from a plurality of images among the plurality of projection images and the plurality of tomographic images, detects an object of interest candidate region estimated to include an object of interest from the synthetic two-dimensional image, and determines whether or not the object of interest is included in the object of interest candidate region on the basis of the plurality of tomographic images.

According to the present disclosure, it is possible to effectively perform the interpretation of the radiographic image.

BRIEF DESCRIPTION OF THE DRAWINGS

FIG. 9 is a flowchart illustrating an example of the flow of the image interpretation support process according to Modification Example 1;

FIG. 10 is a flowchart illustrating an example of the flow of the image interpretation support process according to Modification Example 2;

DETAILED DESCRIPTION

Hereinafter, embodiments of the invention will be described in detail with reference to the drawings. Each of the embodiments does not limit the invention.

Figure 1:
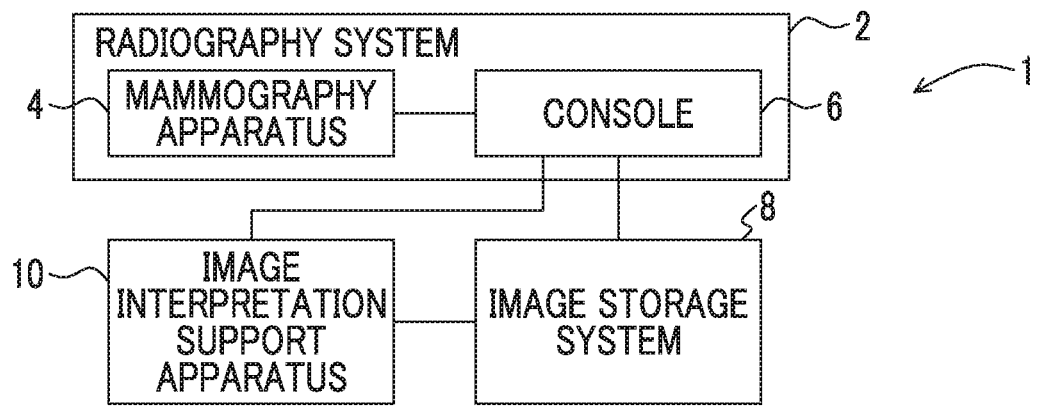
FIG. 1 is a diagram schematically illustrating an example of the overall configuration of a medical system according to an embodiment.

First, an example of the overall configuration of a medical system comprising an image interpretation support apparatus according to the embodiment will be described. FIG. 1 is a diagram illustrating an example of the overall configuration of a medical system 1 according to the embodiment.

As illustrated in FIG. 1, the medical system 1 according to the embodiment comprises a radiography system 2, an image storage system 8, and an image interpretation support apparatus 10.

The radiography system 2 includes a mammography apparatus 4 and a console 6.

The console 6 according to the embodiment has a function of controlling the mammography apparatus 4 using, for example, an imaging order and various information acquired from a radiology information system (RIS) (not illustrated) through a wireless communication local area network (LAN) and instructions given directly by a radiology technician. As an example, in the embodiment, a server computer is used as the console 6.

On the other hand, the mammography apparatus 4 according to the embodiment comprises a radiation source (not illustrated), a radiation detector, or the like. The mammography apparatus 4 irradiates radiation (for example, X-rays) from the radiation source to the breast with the breast of a subject as an object under the control of the console 6, and captures the radiographic image of the breast using the radiation detector. In addition, the mammography apparatus 4 may be an apparatus that captures the image of the breast of the subject not only in a state in which the subject stands up (standing state) but also in a state in which the subject sits on, for example, a chair (including a wheelchair) (sitting state). In the embodiment, a plurality of types of radiographic images, such as a projection image, a tomographic image, and a synthetic two-dimensional image, which will be described in detail later, has been described. However, in a case where the types are collectively referred to without distinguishing the types, they may be simply referred to as the "radiographic images".

In the mammography apparatus 4 according to the embodiment, the plurality of types of imaging can be performed to capture the radiographic images. Specifically, the mammography apparatus 4 performs two types of so-called simple imaging, that is, cranio-caudal (CC) imaging in which the imaging direction is a cranio-caudal direction and medio-lateral oblique (MLO) imaging in which the imaging direction is a medio-lateral oblique direction for the breast.

Further, the mammography apparatus 4 of the embodiment can perform tomosynthesis imaging in which radiation is irradiated to the breast from different irradiation angles by the radiation source, and the projection image is captured at each irradiation angle by the radiation detector.

The image storage system 8 according to the embodiment stores image data of the radiographic image captured by the radiography system 2. The image storage system 8 extracts an image corresponding to a request from, for example, the console 6 and the image interpretation support apparatus 10 from the stored radiographic images and transmits the extracted image to the apparatus which is the request source. A specific example of the image storage system 8 is a picture archiving and communication system (PACS).

The image interpretation support apparatus 10 according to the embodiment is an apparatus for a user such as a doctor to interpret the radiographic image captured by the radiography system 2.

Figure 2:
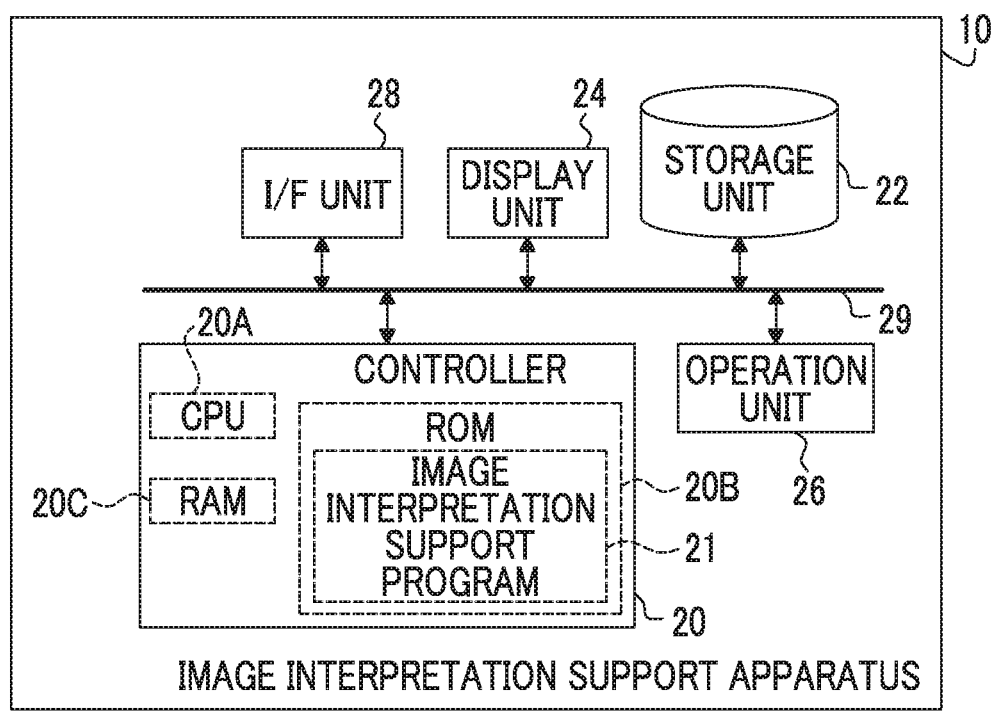
FIG. 2 is a block diagram illustrating an example of the configuration of an image interpretation support apparatus according to the embodiment.

FIG. 2 is a block diagram illustrating an example of the image interpretation support apparatus 10 according to the embodiment. As illustrated in FIG. 2, the image interpretation support apparatus 10 according to the embodiment comprises a controller 20, a storage unit 22, a display unit 24, an operation unit 26, and an I/F (Interface) unit 28. The controller 20, the storage unit 22, the display unit 24, the operation unit 26, and the I/F unit 28 are connected to each other through a bus 29, such as a system bus or a control bus, such that they can transmit and receive various information.

The controller 20 according to this embodiment controls the overall operation of the image interpretation support apparatus 10. The controller 20 comprises a central processing unit (CPU) 20A, a read only memory (ROM) 20B, and a random access memory (RAM) 20C. For example, various programs including an image interpretation support program 21 which is executed by the CPU 20A and performs control related to the interpretation of the radiographic image are stored in a ROM 20B in advance. The RAM 20C temporarily stores various data.

For example, the image data of the radiographic image and various other information are stored in the storage unit 22. Examples of the storage unit 22 include a hard disk drive (HDD) and a solid state drive (SSD). The operation unit 26 is used by the user to input instructions or the like related to the interpretation of the radiographic image. The operation unit 26 is not particularly limited. Examples of the operation unit 26 include various switches, a touch panel, a touch pen, and a mouse. The display unit 24 displays various information including the radiographic image. In addition, the display unit 24 and the operation unit 26 may be integrated into a touch panel display. The I/F unit 28 performs communication of various information including the image data of the radiographic image between the console 6 and the image storage system 8 using wireless communication or wired communication.

Figure 3:
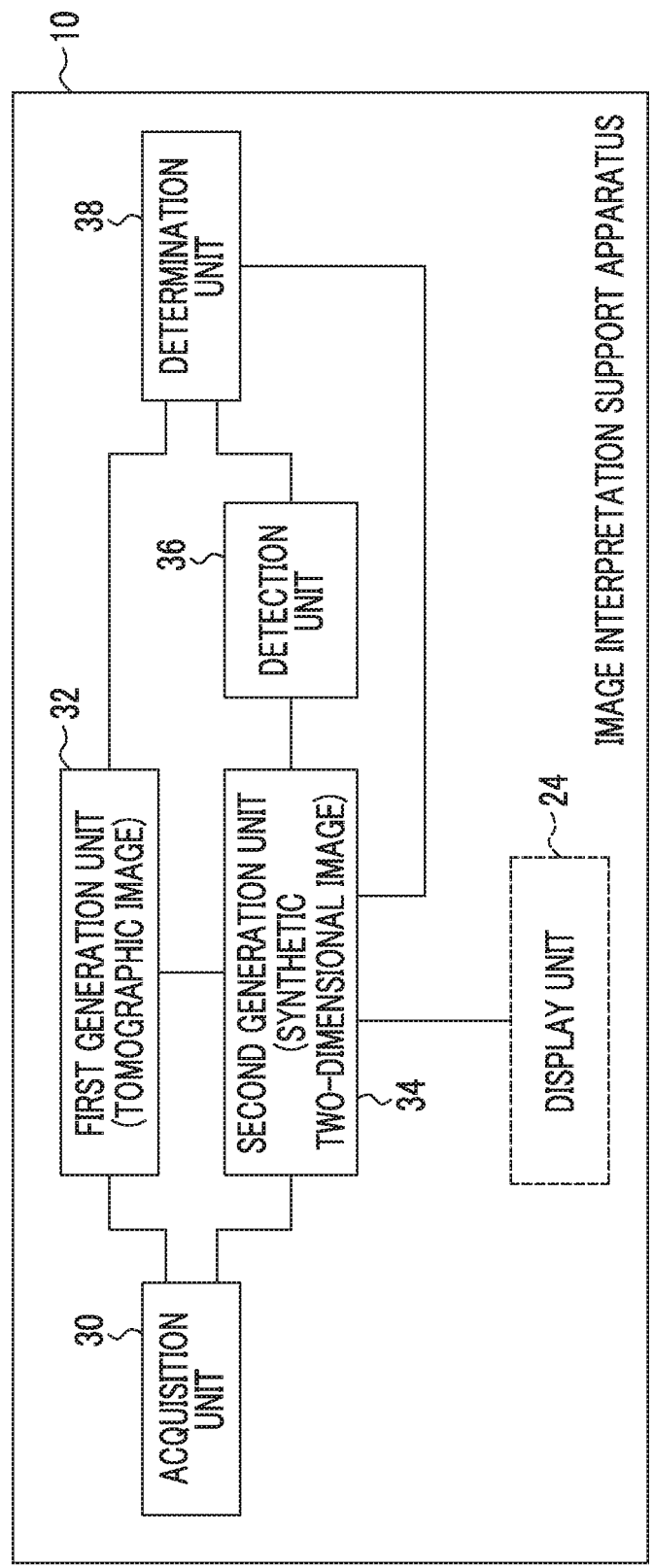
FIG. 3 is a functional block diagram illustrating an example of the function of the image interpretation support apparatus according to the first embodiment.

FIG. 3 is a functional block diagram illustrating an example of the configuration of the image interpretation support apparatus 10 according to the embodiment. As illustrated in FIG. 3, the image interpretation support apparatus 10 of the embodiment comprises an acquisition unit 30, a first generation unit 32, a second generation unit 34, a detection unit 36, and a determination unit 38. As an example, in the image interpretation support apparatus 10 of the embodiment, the CPU 20A of the controller 20 executes the image interpretation support program 21 stored in the ROM 20B and thereby the controller 20 functions as each of the acquisition unit 30, the first generation unit 32, the second generation unit 34, the detection unit 36, and the determination unit 38.

The acquisition unit 30 acquires the plurality of projection images captured by the mammography apparatus 4 and outputs the acquired plurality of projection images to the first generation unit 32 and the second generation unit 34. An acquisition source from which the acquisition unit 30 acquires the plurality of projection images is not limited. For example, the image storage system 8 or the console 6 may be the acquisition source, or in a case where the image is stored in the storage unit 22 in advance, the storage unit 22 may be the acquisition source.

The first generation unit 32 generates a plurality of tomographic images on each of a plurality of tomographic planes of the breast by reconstructing all or a part of the plurality of projection images input from the acquisition unit 30, and outputs the generated plurality of tomographic images to the second generation unit 34 and the determination unit 38.

A method by which the first generation unit 32 generates the tomographic image from the plurality of projection images is not particularly limited. For example, back projection methods such as a filtered back projection (FBP) method or a simple back projection method, alternatively, a known method such as a shift addition method can be used.

The second generation unit 34 generates the synthetic two-dimensional image from a plurality of radiographic images of the plurality of projection images or the plurality of tomographic images. The synthetic two-dimensional image generated by the second generation unit 34 is output to the detection unit 36. The plurality of radiographic images used by the second generation unit 34 to generate the synthetic two-dimensional image are not particularly limited, and for example, it may be determined in advance that all of the plurality of tomographic images are used, or may be selectable by the user. For example, it may be determined in advance according to a method of generating a two-dimensional image.

The tomographic image used by the second generation unit 34 to generate the synthetic two-dimensional image is generated by the first generation unit 32.

A method by which the second generation unit 34 generates the synthetic two-dimensional image is not particularly limited, and a known method can be used. For example, JP2014-128716A discloses a method of generating a synthetic two-dimensional image by projecting a plurality of tomographic images, or at least one of the plurality of tomographic images and at least one of a plurality of projection images in a depth direction in which a tomographic plane in a breast is arranged, or by using a minimum value projection method. Also, for example, JP6208731B discloses a method of generating a synthetic two-dimensional image by reconstructing a plurality of projection images, a plurality of tomographic images, or at least one of the plurality of tomographic images and at least one of the plurality of projection images using any method such as a filtered back projection method, a maximum likelihood reconstruction method, an iterative reconstruction method, a reconstruction method using an algebraic method, or a three-dimensional reconstruction method. Further, for example, U.S. Pat. No. 8,983,156B discloses a method of blending (synthesizing) a region of interest (ROI) detected from a tomographic image with a two-dimensional image to generate the synthetic two-dimensional image.

The detection unit 36 detects an object of interest candidate region estimated to include an object of interest from the synthetic two-dimensional image generated by the second generation unit 34, and outputs a detection result to the determination unit 38. In the embodiment, the "object of interest" is an object of interest to the user who interprets the radiographic image, and includes, for example, a lesion such as a tumor, a so-called abnormal shadow such as calcification, but may be a normal structure. The "object of interest candidate region" is not limited to a region of the object of interest itself, specifically, a region of the image itself corresponding to the image of the object of interest. The "object of interest candidate region" may be a region that is somewhat larger than the object of interest itself. For example, in a case where the object of interest has a circular shape, it may be a rectangular region in which the circular object of interest is inscribed.

A method by which the detection unit 36 detects the object of interest candidate region from the synthetic two-dimensional image is not particularly limited. For example, there is a method of extracting a specific structure representing the object of interest from the synthetic two-dimensional image using an algorithm of a known computer aided diagnosis (hereinafter referred to as CAD). In the algorithm based on CAD, a probability (for example, likelihood) indicating that a pixel in the synthetic two-dimensional image is an object of interest is derived, and in a case where the probability is equal to or more than a predetermined threshold value, it is preferable that the pixel is detected as a pixel configuring the image of the object of interest. Further, for example, a method of extracting the object of interest from the synthetic two-dimensional image by filtering process using a filter for extracting the object of interest may be used.

The determination unit 38 determines whether or not the object of interest is included in the object of interest candidate region obtained as the detection result of the detection unit 36 on the basis of the plurality of tomographic images generated by the first generation unit 32, and outputs a determination result to the second generation unit 34. The details of the method in which the determination unit 38 determines whether or not the object of interest is included in the object of interest candidate region will be described later.

Next, the operation of the image interpretation support apparatus 10 according to the embodiment will be described with reference to the drawings.

Figure 4:
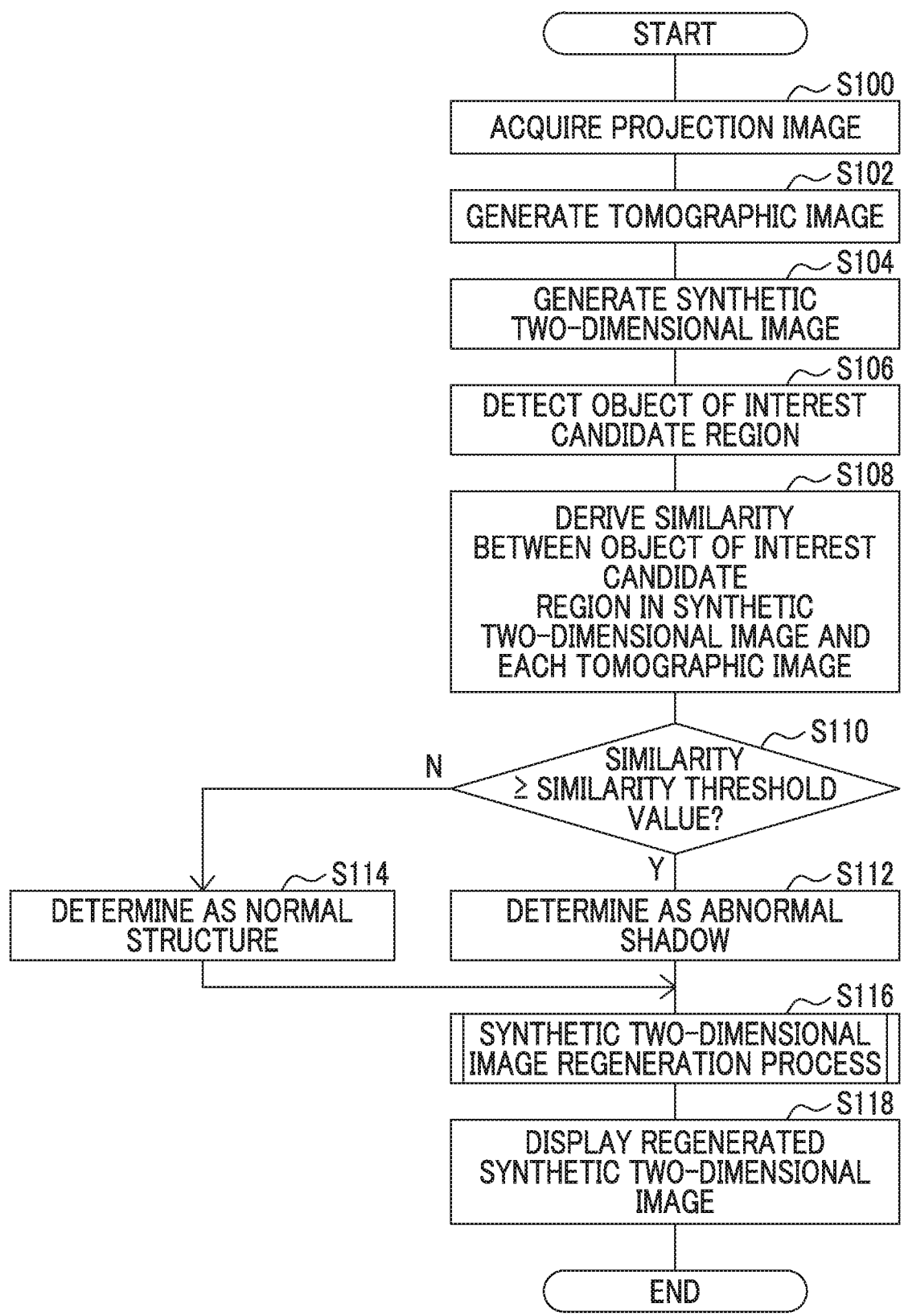
FIG. 4 is a flowchart illustrating an example of the flow of an image interpretation support process of the image interpretation support apparatus according to the embodiment.

For example, in a case where the image interpretation support apparatus 10 according to the embodiment receives an instruction to perform the interpretation performed by the user through the operation unit 26, the CPU 20A of the controller 20 executes the image interpretation support program 21 stored in the ROM 20B to execute an image interpretation support process whose an example is illustrated in FIG. 4. FIG. 4 is a flowchart illustrating an example of the flow of the image interpretation support process of the image interpretation support apparatus 10 according to the embodiment.

In the image interpretation support process illustrated in FIG. 4, first, in Step S100, the acquisition unit 30 acquires the plurality of projection images obtained by imaging subjects to be interpreted, as described above, for example, such as a right breast of the subject according to the instruction of the user.

In the next Step S102, the first generation unit 32 generates the plurality of tomographic images by reconstructing all or a part of the plurality of projection images as described above. In the next Step S104, the second generation unit 34 generates the synthetic two-dimensional image from the plurality of radiographic images of the plurality of projection images or the plurality of tomographic images as described above. In the next Step S106, the detection unit 36 detects the object of interest candidate region from the synthetic two-dimensional image generated in Step S104.

In the next Step S108, the determination unit 38 derives similarity between the image of the object of interest candidate region in the synthetic two-dimensional image and each of the plurality of tomographic images generated in Step S102. A method by which the determination unit 38 derives the similarity is not particularly limited, and a known method can be used. For example, there is a method of deriving the similarity by deriving a normalized cross-correlation with respect to a pixel value of the image of the object of interest candidate region in the synthetic two-dimensional image.

In the next Step S110, the determination unit 38 determines whether or not the similarity derived in Step S108 for each of the plurality of tomographic images is equal to or more than a predetermined similarity threshold value (similarity≥similarity threshold value). That is, the determination unit 38 determines whether or not the tomographic image including the same image as (similar to) the image of the object of interest candidate region in the synthetic two-dimensional image is included in the plurality of tomographic images on the basis of the similarity. Specifically, the determination unit 38 compares the image of the object of interest candidate region in the synthetic two-dimensional image and an image of a corresponding region which is a region of a position corresponding to the object of interest candidate region in the tomographic image, and derives similarity having a higher value as the similarity increases. The similarity threshold value may be determined in advance according to desired accuracy or the like, or may be set and changed by the user or the like.

On the other hand, in a case where there is at least one tomographic image whose similarity is equal to or more than the similarity threshold value, the determination result in Step S110 is "Yes" and the process proceeds to Step S112. In this case, there is the same tomographic image as (similar to) the image of the object of interest candidate region detected from the synthetic two-dimensional image, which indicates that the image of the object of interest that can be detected from the tomographic image is reflected in the synthetic two-dimensional image. Therefore, in Step S112, the determination unit 38 determines that the object of interest candidate region detected from the synthetic two-dimensional image includes an object of interest corresponding to an abnormal shadow, and then proceeds to Step S116.

On the other hand, in a case where there is no tomographic image whose similarity is equal to or more than the similarity threshold value, in other words, in a case where the similarities of all the tomographic images are less than the similarity threshold value (similarity<similarity threshold value), the determination result in Step S110 is "No", and the process proceeds to Step S114. In this case, it is possible that there is no tomographic image including the same image as (similar to) the image to the object of interest candidate region detected from the synthetic two-dimensional image.

Figure 5A:
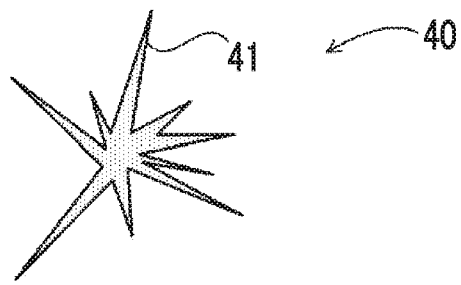
FIG. 5A is a diagram illustrating an example of an abnormal shadow in the case of a specular.

An abnormal shadow called a specular is known in tumors or the like. As illustrated in FIG. 5A, a specular 41 grows while involving a surrounding tissue of the breast, and appears in the radiographic image as an abnormal shadow 40 of a linear structure. The specular 41 can be detected from both the synthetic two-dimensional image and the tomographic image. Therefore, the detection unit 36 detects a region including the specular 41 as the object of interest candidate region of the synthetic two-dimensional image, and the determination unit 38 determines that a tomographic image including the specular 41 exists.

Figure 5B:
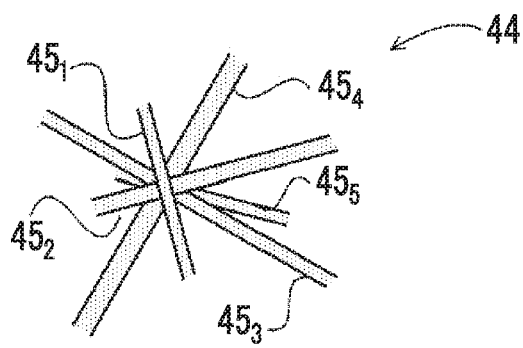
FIG. 5B is a diagram illustrating an example of a normal structure in the case of overlapping a mammary gland.

On the other hand, a structure that looks like a specular due to overlapping edges of a normal structure such as a mammary gland may appear in the synthetic two-dimensional image. For example, as illustrated in FIG. 5B, in a case of a normal structure 44 in a state where a plurality of mammary glands 45₁ to 45₅ overlap each other, since the plurality of mammary glands 45₁ to 45₅ appear in the synthetic two-dimensional image in a state of overlapping, the normal structure 44 have a form similar to that of the specular 41. That is, in a case of interpreting the synthetic two-dimensional image including the normal structure 44, the normal structure 44 may look like the abnormal shadow 40. In addition, the detection unit 36 detects a region including the normal structure 44 that is the mammary glands 45₁ to 45₅ as the object of interest candidate region of the synthetic two-dimensional image.

On the other hand, since the plurality of overlapping mammary glands 45₁ to 45₅ are located at different heights in the breast, each of the plurality of mammary glands 45₁ to 45₅ may appear in different tomographic images, and may not look like the normal structure 44 appearing in the synthetic two-dimensional image. For example, in a case where any one of the mammary glands $45_1$ to $45_5$ appears in one tomographic image, the form does not have the shape of the normal structure 44 appearing in the synthetic two-dimensional image. For this reason, the normal structure 44 is not detected as an abnormal shadow from the tomographic image, and since there is no tomographic image including the normal structure 44, the determination unit 38 determines that there is no tomographic image including the same image as (similar to) the image of the object of interest candidate region.

As described above, in the embodiment, the object of interest candidate region is detected as an abnormal shadow from the synthetic two-dimensional image, but is detected as a normal structure from the tomographic image, the determination result in Step S110 is "No", and the process proceeds to Step S114.

In Step S114, the determination unit 38 determines that the object of interest candidate region detected from the synthetic two-dimensional image includes a normal structure and does not include the object of interest corresponding to an abnormal shadow, and then proceeds to Step S116.

In the next Step S116, the determination unit 38 causes the second generation unit 34 to perform a synthetic two-dimensional image regeneration process (see FIG. 6, which will be described in detail below). The second generation unit 34 reconstructs the plurality of radiographic images of the plurality of projection images and the plurality of tomographic images by the synthetic two-dimensional image regeneration process, and regenerates the synthetic two-dimensional image. Hereinafter, the synthetic two-dimensional image generated by the synthetic two-dimensional image regeneration process is referred to as a "regenerated synthetic two-dimensional image".

In the next Step S118, the second generation unit 34 causes the display unit 24 to display the regenerated synthetic two-dimensional image, and then ends the main image interpretation support process.

Figure 6:
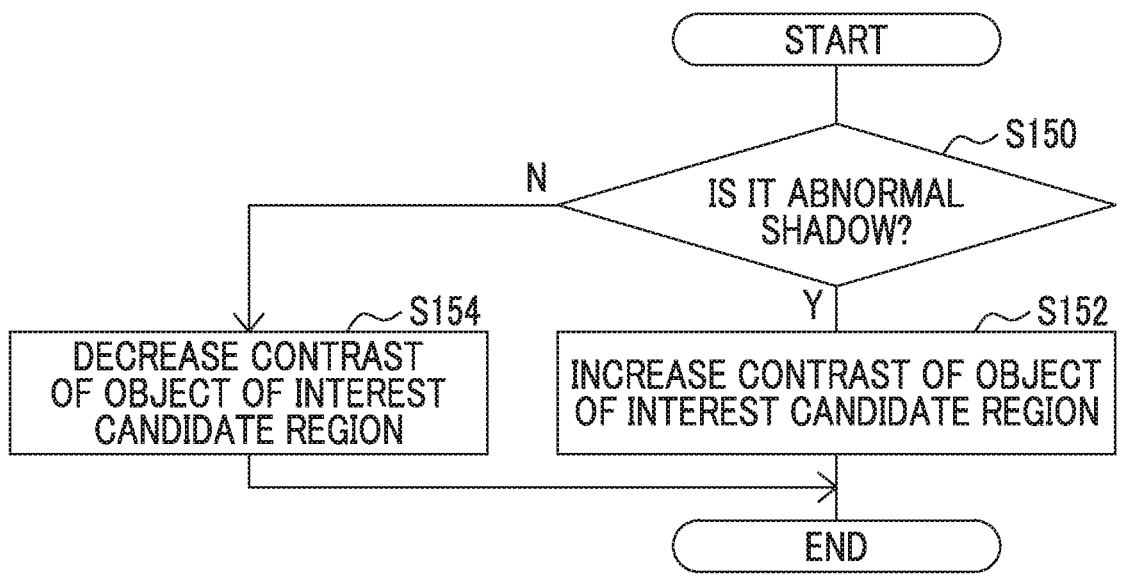
FIG. 6 is a flowchart illustrating an example of the flow of a synthetic two-dimensional image generation process executed in the image interpretation support process.

With reference to FIG. 6, the synthetic two-dimensional image regeneration process executed in Step S116 of the image interpretation support process will be described. FIG. 6 is a flowchart illustrating an example of the flow of the synthetic two-dimensional image regeneration process.

In Step S150, the second generation unit 34 causes the determination unit 38 to determine whether or not the object of interest included in the object of interest candidate region is an abnormal shadow. In a case where the object of interest included in the object of interest candidate region is an abnormal shadow, the determination result in Step S150 is "Yes" and the process proceeds to Step S152.

In Step S152, the second generation unit 34 adjusts a contrast of the object of interest candidate region by increasing a contrast of the image of the object of interest candidate region in the synthetic two-dimensional image by a predetermined degree from contrasts of images of other regions.

Figure 7:
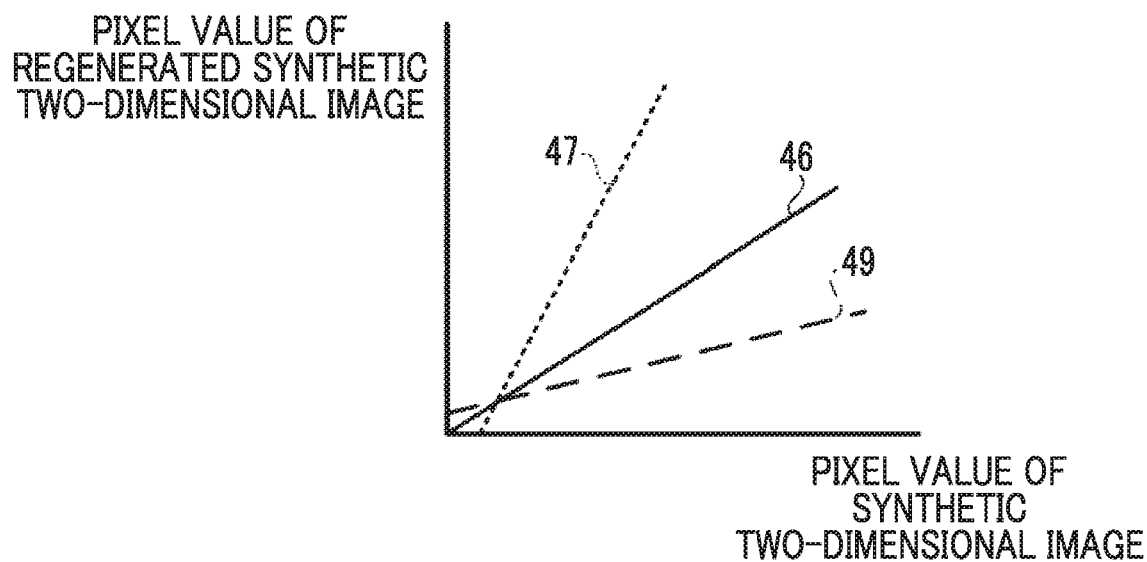
FIG. 7 is a diagram illustrating adjustment of a contrast in a second generation unit according to the embodiment.

For example, the signal of the object of interest candidate region is strengthened and the contrast is increased by changing a correspondence between the pixel value of the image of the object of interest candidate region in the synthetic two-dimensional image (synthetic two-dimensional image generated in Step S104) before regeneration and the pixel value of the image of the object of interest candidate region in the regenerated synthetic two-dimensional image from a correspondence represented by a line 46 in FIG. 7 to a correspondence represented by a line 47 whose inclination is larger than the line 46. The regenerated synthetic two-dimensional image is an image in which the object of interest candidate region is emphasized by increasing the contrast of the object of interest candidate region.

On the other hand, in a case where the object of interest included in the object of interest candidate region is not an abnormal shadow, that is, in a case where a normal structure is included in the object of interest candidate region, the determination result in Step S150 is "No", and the process proceeds to Step S154.

In Step S154, the second generation unit 34 adjusts a contrast of the object of interest candidate region by decreasing a contrast of the image of the object of interest candidate region in the synthetic two-dimensional image by a predetermined degree from contrasts of images of other regions. The second generation unit 34 of the embodiment, as opposed to increasing the contrast in the Step S152, the signal of the object of interest candidate region is weakened and the contrast is decreased by changing the correspondence between the pixel value of the image of the object of interest candidate region in the synthetic two-dimensional image before regeneration and the pixel value of the image of the object of interest candidate region in the regenerated synthetic two-dimensional image from a correspondence represented by the line 46 in FIG. 7 to a correspondence represented by a line 49 whose inclination is smaller than the line 46. The regenerated synthetic two-dimensional image is an image in which the object of interest candidate region is suppressed by decreasing the contrast of the object of interest candidate region. Therefore, in the regenerated synthetic two-dimensional image, a normal structure is suppressed from appearing as an abnormal shadow.

A method by which the second generation unit 34 adjusts the contrast of the image of the object of interest candidate region is not limited, and for example, a known method such as gradation process or frequency process may be used. Further, a degree to which the second generation unit 34 increases or decreases the contrast may be determined in advance from experimental results or the like, or may be specified by the user.

In a case where the regenerated synthetic two-dimensional image whose contrast is adjusted by the process of Step S152 or Step S154 is generated, the synthetic two-dimensional image regeneration process ends, and Step S116 (see FIG. 4) of the image interpretation support process ends.

Figure 8A:
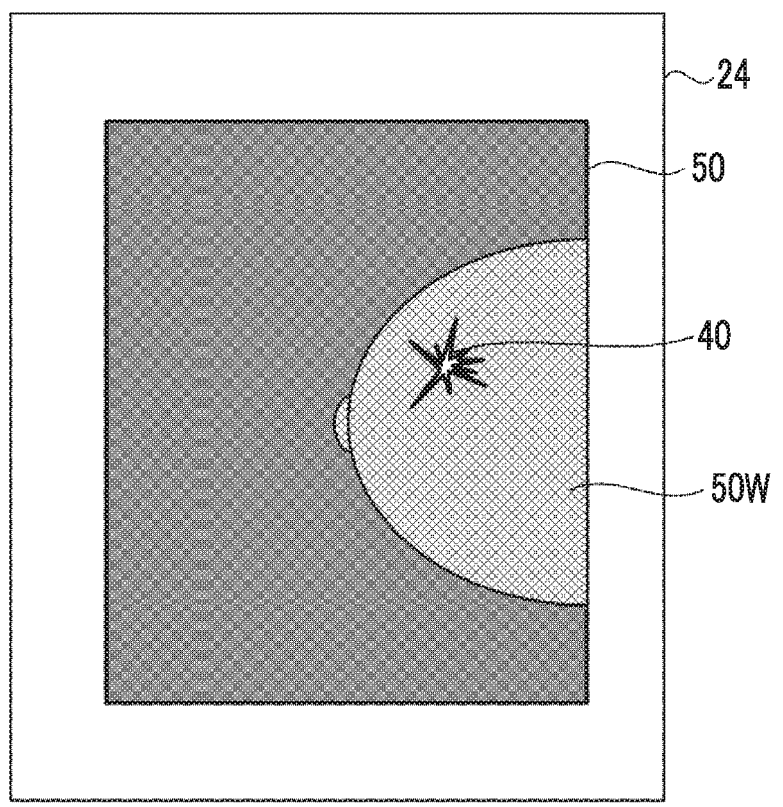
FIG. 8A is a diagram illustrating an example of a regenerated synthetic two-dimensional image including the abnormal shadow displayed on a display unit according to the embodiment.
Figure 8B:
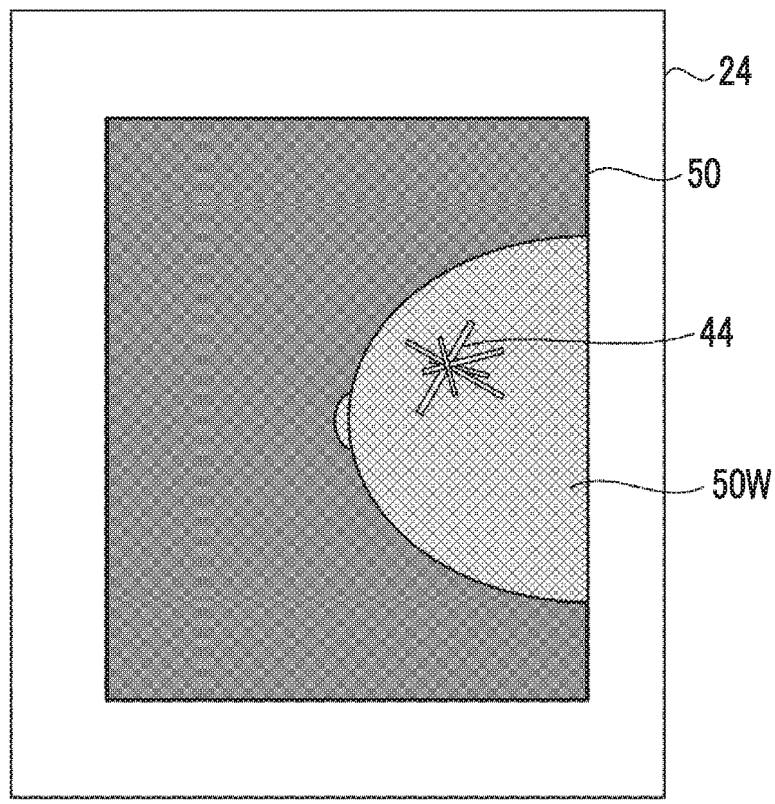
FIG. 8B is a diagram illustrating an example of the regenerated synthetic two-dimensional image including a normal structure displayed on the display unit according to the embodiment.

FIGS. 8A and 8B illustrate an example of a regenerated synthetic two-dimensional image 50 displayed on the display unit 24. The regenerated synthetic two-dimensional image 50 illustrated in FIG. 8A includes a breast image 50W including the object of interest candidate region determined to be the abnormal shadow 40. Further, the regenerated synthetic two-dimensional image 50 illustrated in FIG. 8B includes the breast image 50W including the object of interest candidate region determined to be the normal structure 44. Since the regenerated synthetic two-dimensional image 50 illustrated in FIG. 8A is an image in which the object of interest candidate region determined to be the abnormal shadow 40 is emphasized, it becomes easy for the user who performs an image interpretation to recognize the abnormal shadow 40. On the other hand, since the regenerated synthetic two-dimensional image 50 illustrated in FIG. 8B is an image in which the object of interest candidate region determined to be the normal structure 44 is suppressed, it becomes difficult for the user who performs an image interpretation to recognize the normal structure 44 as a lesion.

In the image interpretation support process, a method by which the determination unit 38 determines whether or not the object of interest included in the object of interest candidate region of the synthetic two-dimensional image is an abnormal shadow or a normal structure is not limited to the method described above, and for example, the methods of Modification Example 1 and Modification Example 2 below may be applied.

Modification Example 1

FIG. 9 is a flowchart illustrating an example of the flow of the image interpretation support process of the image interpretation support apparatus 10 according to the modification example. As illustrated in FIG. 9, the image interpretation support process of the modification example is different from the image interpretation support process of the embodiment (see FIG. 4) in that it has a process of Step S110A located between Step S110 and Step S112.

As illustrated in FIG. 9, in the image interpretation support process of the modification example, in a case where the determination result in Step S110 is "Yes", the process proceeds to Step S110A. In Step S110A, the determination unit 38 determines whether or not an interval between the tomographic images whose similarity with the synthetic two-dimensional image is equal to or more than the similarity threshold value is less than a predetermined interval. The interval between the tomographic images means a distance in a depth direction of a tomography unit indicated by the tomographic image.

In a case where the object of interest included in the object of interest candidate region is determined as an abnormal shadow such as, for example, the specular 41, a thickness of the object of interest is relatively thick, so that there is a tendency that similar images are continuous in the depth direction of the tomography unit. That is, in the case where the object of interest included in the object of interest candidate region is determined to be an abnormal shadow, there is a tendency that a plurality of tomographic images whose similarity with the synthetic two-dimensional image is equal to or more than the similarity threshold value is adjacent to each other. Therefore, the determination unit 38 of the modification example determines whether or not the tomographic image whose similarity with the synthetic two-dimensional image is equal to or more than the similarity threshold value has the tendency, and determines whether or not the object of interest included in the object of interest candidate region of the synthetic two-dimensional image is an abnormal shadow according to the result.

In a case where the interval between the tomographic images whose similarity with the synthetic two-dimensional image is equal to or more than the similarity threshold value is less than the predetermined interval, since it has the above tendency, the determination result in Step S110A is "Yes" and the process proceeds to Step S112. On the other hand, in a case where the interval between the tomographic images whose similarity is equal to or more than the similarity threshold value is not less than the predetermined interval, in other whose, in a case where the interval between the tomographic images whose similarity is equal to or more than the similarity threshold value is equal to or more than the predetermined interval, it does not have the above tendency, and the determination result in Step S110A is "No" and the process proceeds to Step S114. In addition, in a case where there is only one tomographic image whose similarity is equal to or more than the similarity threshold value, the determination result in Step S110A is "No" and the process proceeds to Step S114.

The predetermined interval used in the determination in Step S110A may be determined in advance based on experimental results or the like, may be variable according to the thickness of the tomographic image, or may be specified by the user.

Modification Example 2

FIG. 10 is a flowchart illustrating an example of the flow of the image interpretation support process of the image interpretation support apparatus 10 according to the modification example. As illustrated in FIG. 10, the image interpretation support process of the modification example is different from the image interpretation support process of the embodiment (see FIG. 4) in that Steps S106 to S110 are replaced with Steps S107 to S111.

As illustrated in FIG. 10, in the image interpretation support process of the modification example, in Step S107, the determination unit 38 detects an object of interest estimation region in which the object of interest is estimated to be included from each of the plurality of tomographic images generated in Step S102. A method by which the determination unit 38 detects the object of interest estimation region from the tomographic image is not limited, and for example, a method similar to the method by which the detection unit 36 detects the object of interest candidate region from the synthetic two-dimensional image can be used.

In the next Step S109, the determination unit 38 determines whether or not there is a tomographic image including the object of interest estimation region. In a case where there is no tomographic image including the object of interest, the tomographic image including the object of interest estimation region is not detected in Step S107. In this case, the determination result in Step S109 is "No" and the process proceeds to Step S114. On the other hand, in a case where there is the tomographic image including the object of interest estimation region, the determination result in Step S109 is "Yes" and the process proceeds to Step S111.

In Step S111, the determination unit 38 determines whether or not the object of interest candidate region of the synthetic two-dimensional image overlaps with the object of interest estimation region of the tomographic image. In other words, it is determined whether or not a coordinate position of the object of interest candidate region in the synthetic two-dimensional image matches at least a part of a coordinate position of the object of interest estimation region in the tomographic image. Specifically, the determination unit 38 derives the position of the object of interest candidate region with respect to the breast from the synthetic two-dimensional image, and derives the position of the object of interest estimation region with respect to the breast from the tomographic image. Furthermore, the determination unit 38 determines whether or not at least parts of the object of interest candidate region and the object of interest estimation region overlap each other on the basis of the position of the object of interest candidate region and the position of the object of interest estimation region.

As described above, in a case where the object of interest included in the object of interest candidate region of the synthetic two-dimensional image is determined to be an abnormal shadow, the object of interest is also detected from the tomographic image. In a case where at least parts of the object of interest candidate region of the synthetic two-dimensional image and the object of interest estimation region of the tomographic image overlap each other, since the same object of interest is detected from both the synthetic two-dimensional image and the tomographic image, the object of interest included in the object of interest candidate region corresponds to an abnormal shadow. Therefore, in the case where at least parts of the object of interest candidate region of the synthetic two-dimensional image and the object of interest estimation region of the tomographic image overlap each other, the determination result in Step S111 is "Yes", and the process proceeds to Step S112. On the other hand, in a case where the object of interest candidate region of the synthetic two-dimensional image does not overlap with the object of interest estimation region of the tomographic image, the determination result in Step S111 is "No", and the process proceeds to Step S114.

As described above, in the case where the same object of interest is detected from both the synthetic two-dimensional image and the tomographic image, the determination unit 38 of the modification example determines that the object of interest included in the object of interest candidate region is an abnormal shadow.

Further, the synthetic two-dimensional image generation process (see FIG. 6) performed in Step S116 of the image interpretation support process is not limited to the above-described process, and for example, the methods of the following Modification Examples 3 to 5 may be applied.

Modification Example 3

Figure 11:
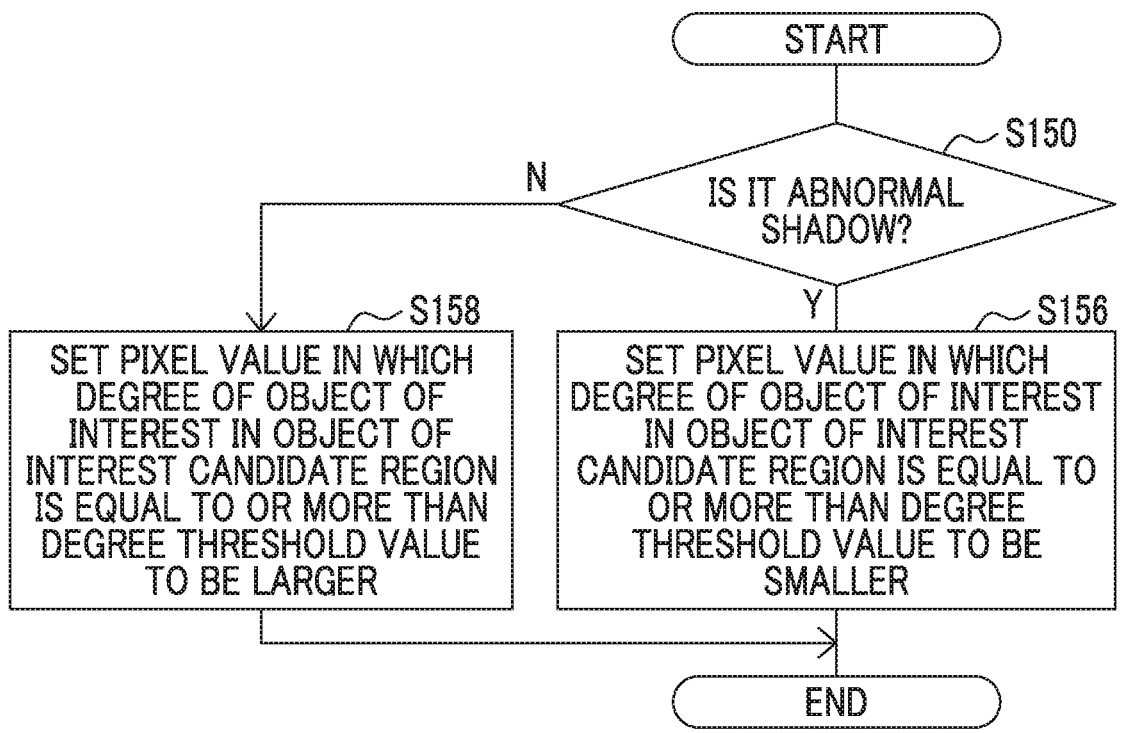
FIG. 11 is a flowchart illustrating an example of the flow of the synthetic two-dimensional image generation process according to Modification Example 3.

FIG. 11 is a flowchart illustrating an example of the flow of the synthetic two-dimensional image generation process of the image interpretation support apparatus 10 according to the modification example. As illustrated in FIG. 11, the synthetic two-dimensional image generation process of the modification example is different from the synthetic two-dimensional image generation process of the embodiment (see FIG. 6) in that Step S152 and Step S154 are replaced with Step S156 and Step S158.

As illustrated in FIG. 11, in the synthetic two-dimensional image generation process of the modification example, in a case where the determination result in step S150 is "Yes", that is, in a case where the object of interest included in the object of interest candidate region is an abnormal shadow, the process proceeds to Step S156. In step S156, the second generation unit 34 ends the synthetic two-dimensional image generation process after setting a pixel value of a pixel in which a degree of an object of interest representing a likelihood of the object of interest is equal to or more than a degree threshold value to be larger than pixel values of other pixels among a plurality of pixels included in the object of interest candidate region.

On the other hand, in a case where the determination result in step S150 is "No", that is, in the case where a normal structure is included in the object of interest candidate region, the process proceeds to Step S158. In step S158, the second generation unit 34 ends the synthetic two-dimensional image generation process after setting a pixel value of a pixel in which a degree of an object of interest representing a likelihood of the object of interest is equal to or more than a degree threshold value to be smaller than pixel values of other pixels among the plurality of pixels included in the object of interest candidate region.

As described above, in the synthetic two-dimensional image generation process of the modification example, in the case where the object of interest is an abnormal shadow, the second generation unit 34 generates the regenerated synthetic two-dimensional image in which the object of interest is emphasized by setting the pixel value of the pixel representing the object of interest to be larger. In addition, in the case where a normal structure is included in the object of interest candidate region, the second generation unit 34 generates the regenerated synthetic two-dimensional image in which the object of interest is suppressed by setting the pixel value of the pixel representing the object of interest to be smaller. According to the modification example, a regenerated synthetic two-dimensional image that looks more natural can be generated.

A method by which the second generation unit 34 derives the degree of the object of interest is not limited. For example, as described above, in a case where the detection unit 36 derives a probability (likelihood) representing the object of interest for each pixel and detects the object of interest candidate region from the synthetic two-dimensional image, the probability may be used as the degree of the object of interest.

Further, in the modification example, an aspect in which the pixel value is set to be larger or smaller in a case where the degree of the object of interest is equal to or more than the degree threshold value has been described, but it is not limited to the aspect, and for example, the pixel value may be set to be larger or smaller as the degree of the object of interest increases.

Modification Example 4

Figure 12:
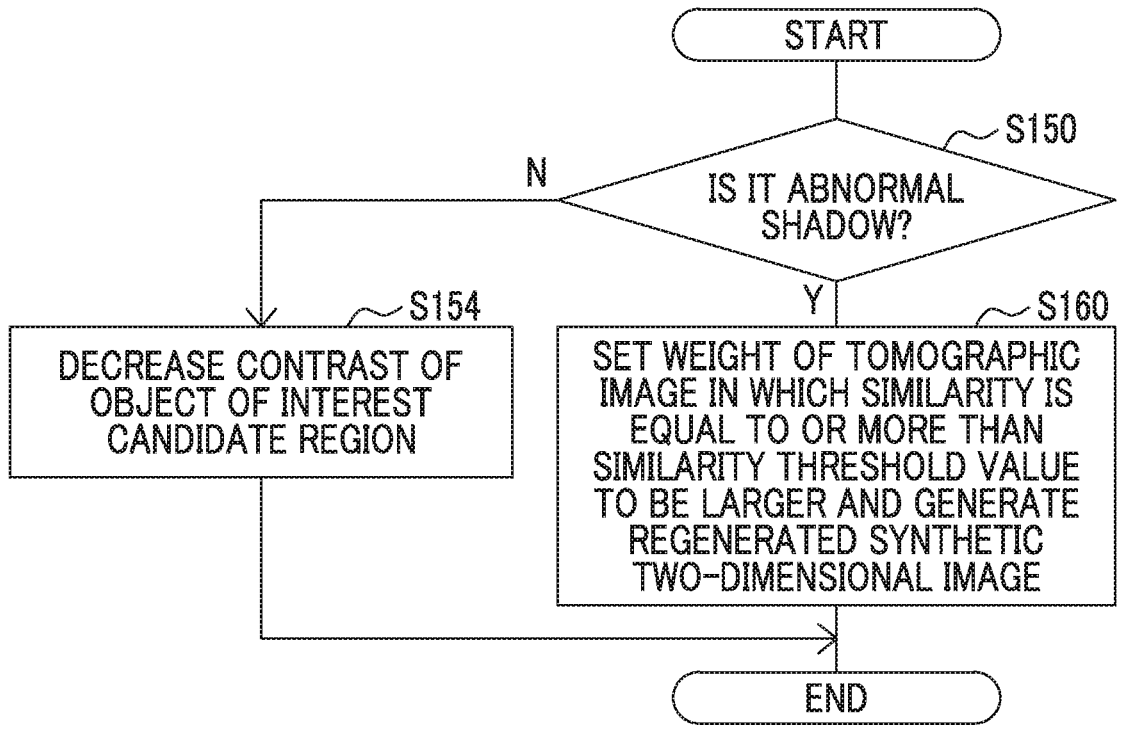
FIG. 12 is a flowchart illustrating an example of the flow of the synthetic two-dimensional image generation process according to Modification Example 4.

The modification example is preferably applied to the case where similarity between the image of the object of interest candidate region in the synthetic two-dimensional image and each of the plurality of tomographic images is derived as in the embodiment and Modification Example 1. FIG. 12 is a flowchart illustrating an example of the flow of the synthetic two-dimensional image generation process of the image interpretation support apparatus 10 according to the modification example. As illustrated in FIG. 12, the synthetic two-dimensional image generation process of the modification example is different from the synthetic two-dimensional image generation process of the embodiment (see FIG. 6) in that Step S152 is replaced with Step S160.

As illustrated in FIG. 12, in the synthetic two-dimensional image generation process of the modification example, in a case where the determination result in step S150 is "Yes", that is, in a case where the object of interest included in the object of interest candidate region is an abnormal shadow, the process proceeds to Step S160. In step S160, the second generation unit 34 ends the synthetic two-dimensional image generation process after setting the weight of the tomographic image in which the similarity is equal to or more than the similarity threshold value to be larger than those of other images and generating the regenerated synthetic two-dimensional image among the plurality of images used for the regenerated synthetic two-dimensional image.

Therefore, in the synthetic two-dimensional image generation process of the modification example, in the case where the object of interest is an abnormal shadow, the second generation unit 34 generates the regenerated synthetic two-dimensional image in which the object of interest is emphasized by setting the weight of the tomographic image including the object of interest to be larger and generating the regenerated synthetic two-dimensional image.

There is no limitation on how to weight. For example, in a case where there are a plurality of tomographic images having similarity threshold value or more, weighting may be performed using a uniform value larger than other images, or weighting may be increased as the similarity threshold value increases.

Modification Example 5

Figure 13:
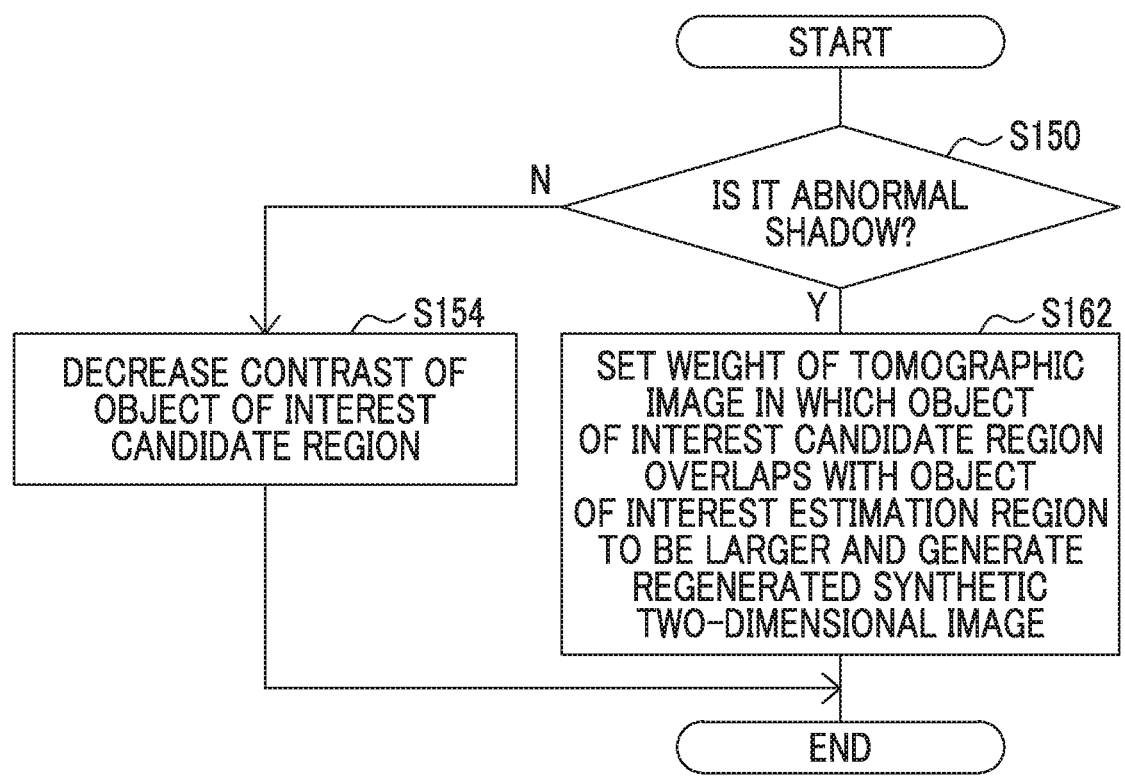
FIG. 13 is a flowchart illustrating an example of the flow of the synthetic two-dimensional image generation process according to Modification Example 5.

The modification example is applied to a case where the object of interest estimation region is detected from a tomographic image as in Modification Example 2. FIG. 13 is a flowchart illustrating an example of the flow of the synthetic two-dimensional image generation process of the image interpretation support apparatus 10 according to the modification example. As illustrated in FIG. 13, the synthetic two-dimensional image generation process of the modification example is different from the synthetic two-dimensional image generation process of the embodiment (see FIG. 6) in that Step S152 is replaced with Step S162.

As illustrated in FIG. 13, in the synthetic two-dimensional image generation process of the modification example, in a case where the determination result in step S150 is "Yes", that is, in a case where the object of interest included in the object of interest candidate region is an abnormal shadow, the process proceeds to Step S162. In step S162, the second generation unit 34 ends the synthetic two-dimensional image generation process after setting the weight of the tomographic image in which the object of interest candidate region of the synthetic two-dimensional image overlaps with the object of interest estimation region to be larger than those of other images and generating the regenerated synthetic two-dimensional image among the plurality of images used for the regenerated synthetic two-dimensional image.

Therefore, in the synthetic two-dimensional image generation process of the modification example, in the case where the object of interest is an abnormal shadow, the second generation unit 34 generates the regenerated synthetic two-dimensional image in which the object of interest is emphasized by setting the weight of the tomographic image including the object of interest to be larger and generating the regenerated synthetic two-dimensional image.

There is no limitation on how to weight. For example, the weighting may be increased as a ratio of the overlapping of the object of interest candidate region and the object of interest estimation region increases.

Figure 14A:
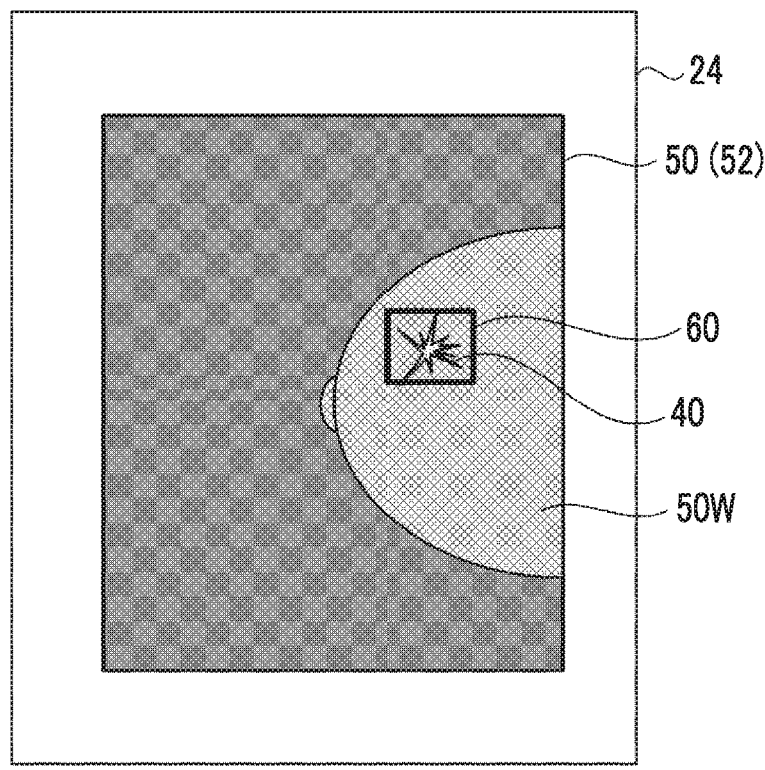
FIG. 14A is a diagram illustrating another example of the regenerated synthetic two-dimensional image including the abnormal shadow displayed on the display unit according to the embodiment.
Figure 14B:
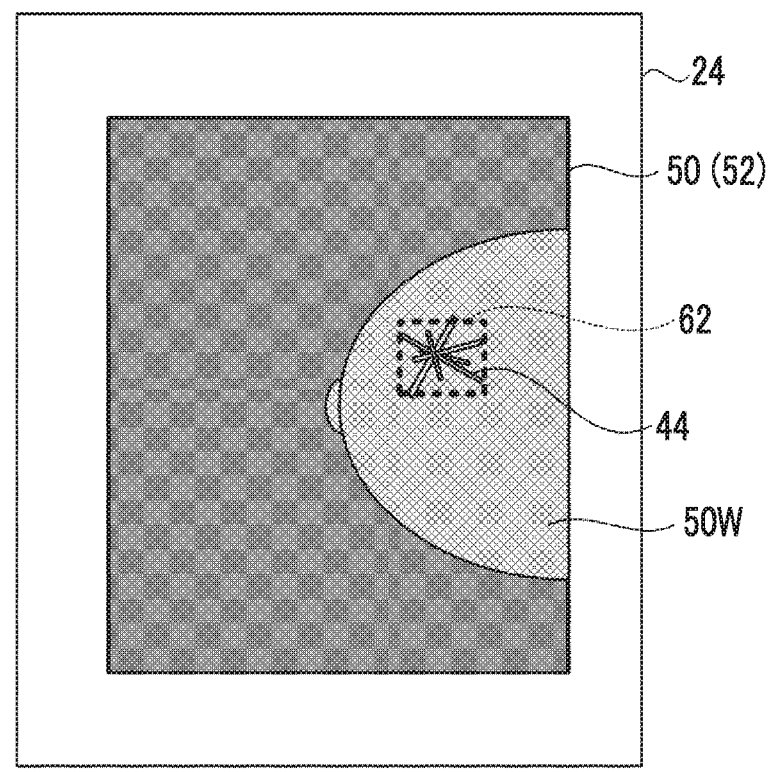
FIG. 14B is a diagram illustrating another example of the regenerated synthetic two-dimensional image including a normal structure displayed on the display unit according to the embodiment.

Further, a radiographic image displayed on the display unit 24 by the image interpretation support apparatus 10 is not limited to the above-described regenerated synthetic two-dimensional image (see FIGS. 8A and 8B). For example, as illustrated in FIGS. 14A and 14B, the second generation unit 34 may display the regenerated synthetic two-dimensional image 50 with marks 60 and 62 indicating the object of interest candidate region on the display unit 24. FIG. 14A illustrates an example of an aspect in which the mark 60 representing the object of interest candidate region including the object of interest which is the abnormal shadow 40 is displayed on the regenerated synthetic two-dimensional image. In addition, FIG. 14B illustrates an example of an aspect in which the mark 62 representing the object of interest candidate region including the normal structure 44 is displayed on the regenerated synthetic two-dimensional image. As illustrated in FIGS. 14A and 14B, it becomes easier for an interpreter to recognize whether or not it is the abnormal shadow 40 or the normal structure 44 by making a line type representing the mark different, for example, the mark 60 representing an object of interest candidate region including the object of interest which is the abnormal shadow 40 and the mark 62 representing the object of interest candidate region including the normal structure 44. In the case where the line type is made different, it is not limited to FIGS. 14A and 14B. For example, a color representing the line may be changed, or the line may be changed depending on whether or not the line is blinked.

Also, as illustrated in FIGS. 14A and 14B, in a case where the mark 60 representing an object of interest candidate region including the object of interest which is the abnormal shadow 40 and the mark 62 representing the object of interest candidate region including the normal structure 44 are displayed, the synthetic two-dimensional image displayed on the display unit 24 by the second generation unit 34 is not limited to the regenerated synthetic two-dimensional image 50. For example, in step S118 of the image interpretation support process (see FIG. 4), the synthetic two-dimensional image 52 generated in step S104 may be displayed on the display unit 24 instead of the regenerated synthetic two-dimensional image 50.

As described above, the image interpretation support apparatus 10 of each of the embodiments comprises an acquisition unit 30, a first generation unit 32, a second generation unit 34, a detection unit 36, and a determination unit 38. The acquisition unit 30 acquires the plurality of projection images obtained by tomosynthesis imaging in which radiation is irradiated to the breast from different irradiation angles by the radiation source, and the projection image is captured at each irradiation angle by the radiation detector. The first generation unit 32 generates the plurality of tomographic images on each of a plurality of tomographic planes of the breast from the plurality of projection images. The second generation unit 34 generates the synthetic two-dimensional image from the plurality of images of the plurality of projection images or the plurality of tomographic images. The detection unit 36 detects the object of interest candidate region estimated to include the object of interest from the synthetic two-dimensional image. The determination unit 38 determines whether or not the object of interest is included in the object of interest candidate region of interest on the basis of the plurality of tomographic images.

By having the above configuration, the image interpretation support apparatus 10 of the embodiment can determine that the object of interest is not included in a case where the object of interest candidate region is detected from the synthetic two-dimensional image, even though the object of interest such as an abnormal shadow is not actually included. For example, even in a case where the object of interest candidate region including a structure that looks like a specular is detected from the synthetic two-dimensional image in which the structure that looks like the specular by overlapping of the edges of normal structures such as the mammary gland appears, it can be determined that the specular is not included. Therefore, in a case of interpreting the synthetic two-dimensional image or the regenerated synthetic two-dimensional image, it is possible to recognize whether or not the object of interest is actually included, in particular, whether it is an abnormal shadow or a normal structure without referring to the tomographic image.

Accordingly, by having the above configuration, in the image interpretation support apparatus 10 of the embodiment, the number of radiographic images to be interpreted can be reduced, so that the interpretation can be made more efficient.

In the embodiment, the image interpretation support process in a case where one object of interest candidate region is detected from the synthetic two-dimensional image has been described, but in a case where a plurality of object of interest candidate regions are detected, the determination unit 38 may determine whether or not each of the plurality of object of interest candidate regions includes the object of interest (abnormal shadow).

In addition, an aspect in which the regenerated synthetic two-dimensional image is displayed on the display unit 24 of the image interpretation support apparatus 10 of the embodiment has been described, but a display apparatus that displays the regenerated synthetic two-dimensional image is not limited to the display unit 24. For example, the regenerated synthetic two-dimensional image may be displayed on the display unit of the console 6.

Further, in the embodiment, an aspect in which the same apparatus (the image interpretation support apparatus 10) comprises the acquisition unit 30, the first generation unit 32, the second generation unit 34, the detection unit 36, and the determination unit 38 has been described, but it is not limited to the aspect, and for example, each unit may be provided in different apparatuses.

In each of the above-described embodiments, for example, the following various processors can be used as the hardware structure of processing units executing various processes such as the acquisition unit 30, the first generation unit 32, the second generation unit 34, the detection unit 36, and the determination unit 38. The various processors include, for example, a programmable logic device (PLD), such as a field-programmable gate array (FPGA), that is a processor whose circuit configuration can be changed after manufacture and a dedicated electric circuit, such as an application specific integrated circuit (ASIC), that is a processor having a dedicated circuit configuration designed to execute a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

As an example of configuring a plurality of processing units with one processor, first, as represented by computers such as a client and a server, there is a form in which one processor is configured by a combination of one or more CPUs and software, and the processor functions as a plurality of processing units. A second example of the configuration is an aspect in which a processor that implements the functions of the entire system including a plurality of processing units using one integrated circuit (IC) chip is used. A representative example of the aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In the embodiment, an aspect in which the image interpretation support program 21 is stored (installed) in the ROM 20B in advance has been described, but, it is not limited thereto. The image interpretation support program 21 may be recorded on a recording medium, such as a compact disc read only memory (CD-ROM), a digital versatile disc read only memory (DVD-ROM), or a universal serial bus (USB) memory, and then provided. In addition, the image interpretation support program 21 may be downloaded from an external apparatus through the network.

For example, the configurations and operations of the medical system 1, the radiography system 2, and the image interpretation support apparatus 10 described in each of the above-described embodiments are illustrative and may be changed according to the situation, without departing from the scope and spirit of the invention. In addition, the above-described embodiments may be appropriately combined with each other.

What is claimed is:

1. An image interpretation support apparatus comprising: a processor that is configured to:
   acquire a plurality of projection images obtained by tomosynthesis imaging in which a radiation is irradiated to a breast from different irradiation angles by a radiation source and a projection image is captured at each irradiation angle by a radiation detector;
   generate a plurality of tomographic images on each of a plurality of tomographic planes of the breast from the plurality of projection images;
   generate a synthetic two-dimensional image from a plurality of images among the plurality of projection images and the plurality of tomographic images;
   detect an object of interest candidate region estimated to include an object of interest from the synthetic two-dimensional image; and
   determine whether or not the object of interest is included in the object of interest candidate region on the basis of the plurality of tomographic images, wherein:
   if it is determined that the object of interest included in the object of interest candidate region is an abnormal shadow, a re-generated synthetic two-dimensional image is re-generated, in which a contrast of image of the object of interest candidate region is increased, from the synthetic two-dimensional image; and
   if it is determined that the object of interest included in the object of interest candidate region is not an abnormal shadow, a re-generated synthetic two-dimensional image is re-generated, in which a contrast of image of the object of interest candidate region is decreased, from the synthetic two-dimensional image.

2. The image interpretation support apparatus according to claim 1,
   wherein the processor is further configured to determine whether or not the object of interest is included in the object of interest candidate region on the basis of a comparison result obtained by comparing an image of the object of interest candidate region in the synthetic two-dimensional image and an image of a corresponding region corresponding to the object of interest candidate region in the tomographic image.

3. The image interpretation support apparatus according to claim 2,
   wherein, in a case where a similarity between the image of the corresponding region in each of the plurality of tomographic images and the image of the object of interest candidate region is less than a similarity threshold value, the processor is further configured to determine that the object of interest is not included in the object of interest candidate region.

4. The image interpretation support apparatus according to claim 3,
   wherein, in a case where the plurality of tomographic images include a tomographic image in which the similarity is equal to or more than the similarity threshold value, the processor is further configured to generate a regenerated synthetic two-dimensional image resynthesized from the plurality of images including at least the tomographic image in which the similarity is equal to or more than the similarity threshold value and having a weight of the tomographic image in which the similarity is equal to or more than the similarity threshold value larger than those of other images.

5. The image interpretation support apparatus according to claim 4,
wherein the processor is further configured to perform a control to cause a display to display the regenerated synthetic two-dimensional image which is resynthesized.

6. The image interpretation support apparatus according to claim 2,
wherein, in a case where the plurality of tomographic images include a tomographic image in which a similarity between the image of the corresponding region and the image of the object of interest candidate region is equal to or more than a similarity threshold value, the processor is further configured to determine that the object of interest is included in the object of interest candidate region.

7. The image interpretation support apparatus according to claim 1,
wherein the processor is further configured to detect an object of interest estimation region estimated to include the object of interest from each of the plurality of tomographic images, and the processor is further configured to determine whether or not the object of interest is included in the object of interest candidate region on the basis of a position of the object of interest candidate region with respect to an image of the breast in the synthetic two-dimensional image and a position of the object of interest estimation region with respect to an image of the breast in the tomographic image.

8. The image interpretation support apparatus according to claim 7,
wherein, in a case where the object of interest estimation region is not detected from each of the plurality of tomographic images, or in a case where the object of interest candidate region does not overlap with the object of interest estimation region, the processor is further configured to determine that the object of interest is not included in the object of interest candidate region.

9. The image interpretation support apparatus according to claim 7,
wherein the processor is further configured to determine that the object of interest is included in the object of interest candidate region in a case where at least parts of the object of interest candidate region or the object of interest estimation region overlap each other.

10. The image interpretation support apparatus according to claim 7,
wherein, in a case of including a tomographic image in which at least a part of the object of interest estimation region overlaps with the object of interest candidate region, the processor is further configured to generate a regenerated synthetic two-dimensional image resynthesized from the plurality of images including at least the tomographic image in which the at least a part of the object of interest estimation region overlaps with the object of interest candidate region, and having a weight of the tomographic image in which at least the part overlaps with the object of interest candidate region larger than other images.

11. The image interpretation support apparatus according to claim 1,
wherein, in a case where the processor determines that the object of interest is included in the object of interest candidate region, the processor is further configured to set a contrast of the object of interest candidate region in the synthetic two-dimensional image to be stronger than contrasts of other regions.

12. The image interpretation support apparatus according to claim 1,
wherein, in a case where the processor determines that the object of interest is not included in the object of interest candidate region, the processor is further configured to set a contrast of the object of interest candidate region in the synthetic two-dimensional image to be weaker than contrasts of other regions.

13. The image interpretation support apparatus according to claim 1,
wherein, in a case where the processor determines that the object of interest is included in the object of interest candidate region, the processor is further configured to set a pixel value of a pixel in which a degree of an object of interest representing a likelihood of the object of interest is equal to or more than a degree threshold value to be larger than pixel values of other pixels among pixels of the object of interest candidate region.

14. The image interpretation support apparatus according to claim 1,
wherein, in a case where the processor determines that the object of interest is not included in the object of interest candidate region, the processor is further configured to set a pixel value of a pixel in which a degree of an object of interest representing a likelihood of the object of interest is equal to or more than a degree threshold value to be smaller than pixel values of other pixels among pixels of the object of interest candidate region.

15. The image interpretation support apparatus according to claim 1, wherein the processor is further configured to determine whether or not the object of interest included in the object of interest candidate region is an abnormal shadow.

16. An image interpretation support method executed by a computer, the method comprising:
acquiring a plurality of projection images obtained by tomosynthesis imaging in which a radiation is irradiated to a breast from different irradiation angles by a radiation source and a projection image is captured at each irradiation angle by a radiation detector;
generating a plurality of tomographic images on each of a plurality of tomographic planes of the breast from the plurality of projection images;
generating a synthetic two-dimensional image from a plurality of images among the plurality of projection images and the plurality of tomographic images;
detecting an object of interest candidate region estimated to include an object of interest from the synthetic two-dimensional image; and
determining whether or not the object of interest is included in the object of interest candidate region on the basis of the plurality of tomographic images, wherein:
if it is determined that the object of interest included in the object of interest candidate region is an abnormal shadow, a re-generated synthetic two-dimensional image is re-generated, in which a contrast of image of the object of interest candidate region is increased, from the synthetic two-dimensional image; and if it is determined that the object of interest included in the object of interest candidate region is not an abnormal shadow, a re-generated synthetic two-dimensional image is re-generated, in which a contrast of image of the object of interest candidate region is decreased, from the synthetic two-dimensional image.

17. A non-transitory computer-readable storage medium storing an image interpretation support program for causing a computer to execute a process, the process comprising:

acquiring a plurality of projection images obtained by tomosynthesis imaging in which a radiation is irradiated to a breast from different irradiation angles by a radiation source and a projection image is captured at each irradiation angle by a radiation detector;

generating a plurality of tomographic images on each of a plurality of tomographic planes of the breast from the plurality of projection images;

generating a synthetic two-dimensional image from a plurality of images among the plurality of projection images and the plurality of tomographic images;

detecting an object of interest candidate region estimated to include an object of interest from the synthetic two-dimensional image; and determining whether or not the object of interest is included in the object of interest candidate region on the basis of the plurality of tomographic images, wherein:

if it is determined that the object of interest included in the object of interest candidate region is an abnormal shadow, a re-generated synthetic two-dimensional image is re-generated, in which a contrast of image of the object of interest candidate region is increased, from the synthetic two-dimensional image; and if it is determined that the object of interest included in the object of interest candidate region is not an abnormal shadow, a re-generated synthetic two-dimensional image is re-generated, in which a contrast of image of the object of interest candidate region is decreased, from the synthetic two-dimensional image.

* * * * *